United States Patent [19]
Laufer et al.

[11] Patent Number: 5,609,598
[45] Date of Patent: Mar. 11, 1997

[54] METHOD AND APPARATUS FOR MINIMALLY INVASIVE TREATMENT OF CHRONIC VENOUS INSUFFICIENCY

[75] Inventors: Michael D. Laufer; H. DuBose Montgomery, both of Menlo Park, Calif.

[73] Assignee: VNUS Medical Technologies, Inc., Menlo Park, Calif.

[21] Appl. No.: 367,063

[22] Filed: Dec. 30, 1994

[51] Int. Cl.⁶ .................................................. A61B 17/10
[52] U.S. Cl. ............................................... 606/142; 623/2
[58] Field of Search .................................. 606/142, 143; 623/2

[56] References Cited

U.S. PATENT DOCUMENTS

| | | | |
|---|---|---|---|
| 3,326,216 | 6/1967 | Wood . | |
| 3,837,345 | 9/1974 | Matar | 128/305 |
| 4,042,979 | 8/1977 | Angell | 3/1.5 |
| 4,056,854 | 11/1977 | Boretos et al. . | |
| 4,655,217 | 4/1987 | Reed | 128/305 |
| 4,791,913 | 12/1988 | Maloney | 128/6 |
| 4,796,629 | 1/1989 | Grayzel | 128/344 |
| 4,851,001 | 7/1989 | Taheri | 623/2 |
| 4,994,077 | 2/1991 | Dobben | 623/2 |
| 5,061,240 | 10/1991 | Cherian | 604/96 |
| 5,147,385 | 9/1992 | Beck et al. . | |
| 5,147,389 | 2/1992 | Lane | 623/2 |
| 5,221,649 | 5/1993 | Kohler et al. | 606/139 |
| 5,358,518 | 10/1994 | Camilli | 623/2 |
| 5,375,612 | 12/1994 | Chottenceau et al. | 128/899 |
| 5,395,381 | 5/1995 | Green et al. | 606/143 |
| 5,395,384 | 5/1995 | Duthoit | 606/159 |
| 5,413,584 | 5/1995 | Schulze | 606/219 |
| 5,445,167 | 8/1995 | Yoon | 606/143 |

FOREIGN PATENT DOCUMENTS

| | | |
|---|---|---|
| 0338994 | 10/1989 | European Pat. Off. . |
| WO91/17720 | 11/1991 | WIPO . |

OTHER PUBLICATIONS

"Total opening valves for a ventricular prosthesis", W. Lenne et al., *Medical and Biological Engineering*, vol. 13, Jul. 1975, pp. 509–517.

Primary Examiner—Michael Powell Buiz
Assistant Examiner—Mark S. Leonardo
Attorney, Agent, or Firm—Fulwider Patton Lee & Utecht, LLP

[57] ABSTRACT

The invention is embodied in an appliance or a prosthesis and a delivery catheter for use in a vein for minimally invasive treatment of chronic venous insufficiency. The system and method of the invention eliminate the need for open surgical valve repair procedures, obviate the need for arm vein transplantation into the leg, and allow patients to return to their former active lifestyles without the limitations currently associated with the treatment of this condition. An incompetent valve to be repaired is identified by injected contrast through the delivery catheter or similar means and the catheter is positioned at that valve, a clip appliance or similar prosthesis is deployed from the catheter and affixed to the valve. Next, the delivery catheter is repositioned and appliances or prostheses are deployed on sequentially lower valves until all desired valves are repaired and functionally competent.

10 Claims, 8 Drawing Sheets

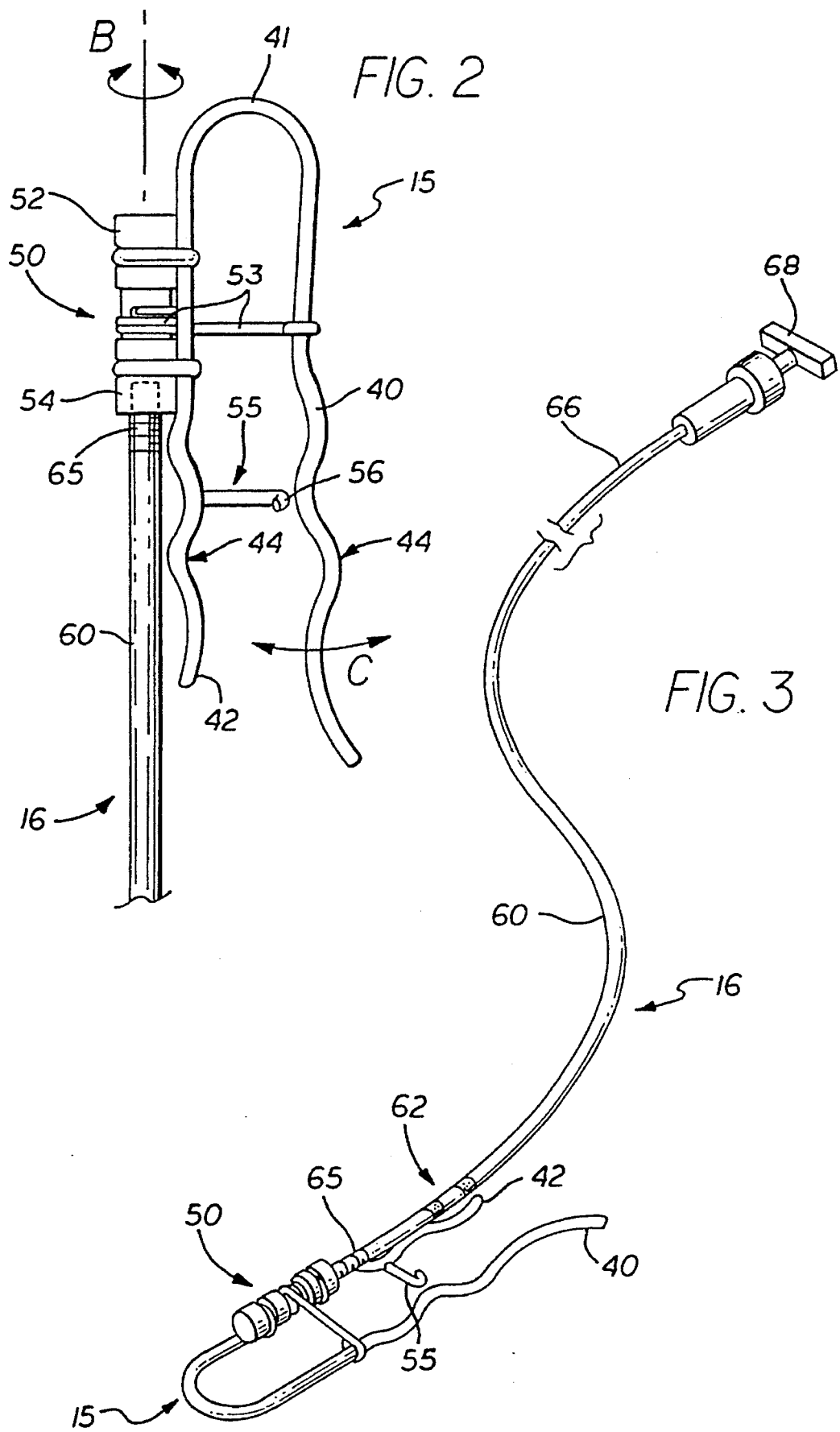

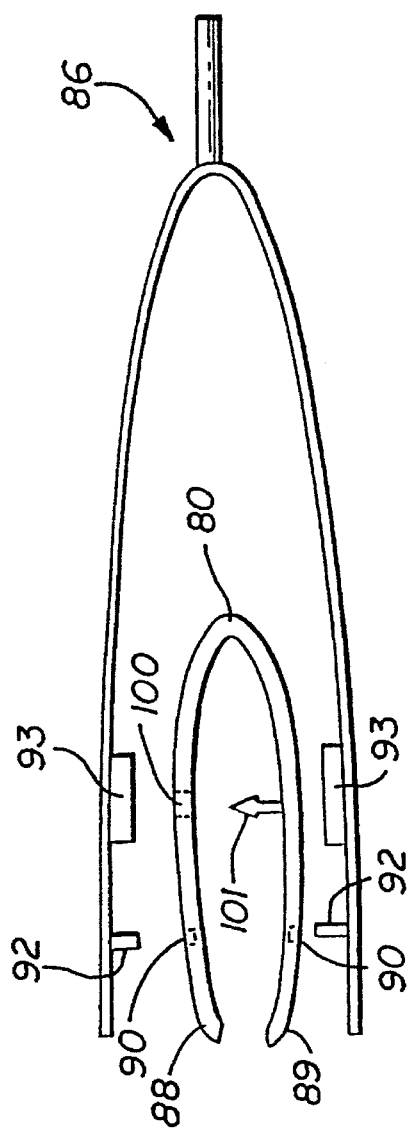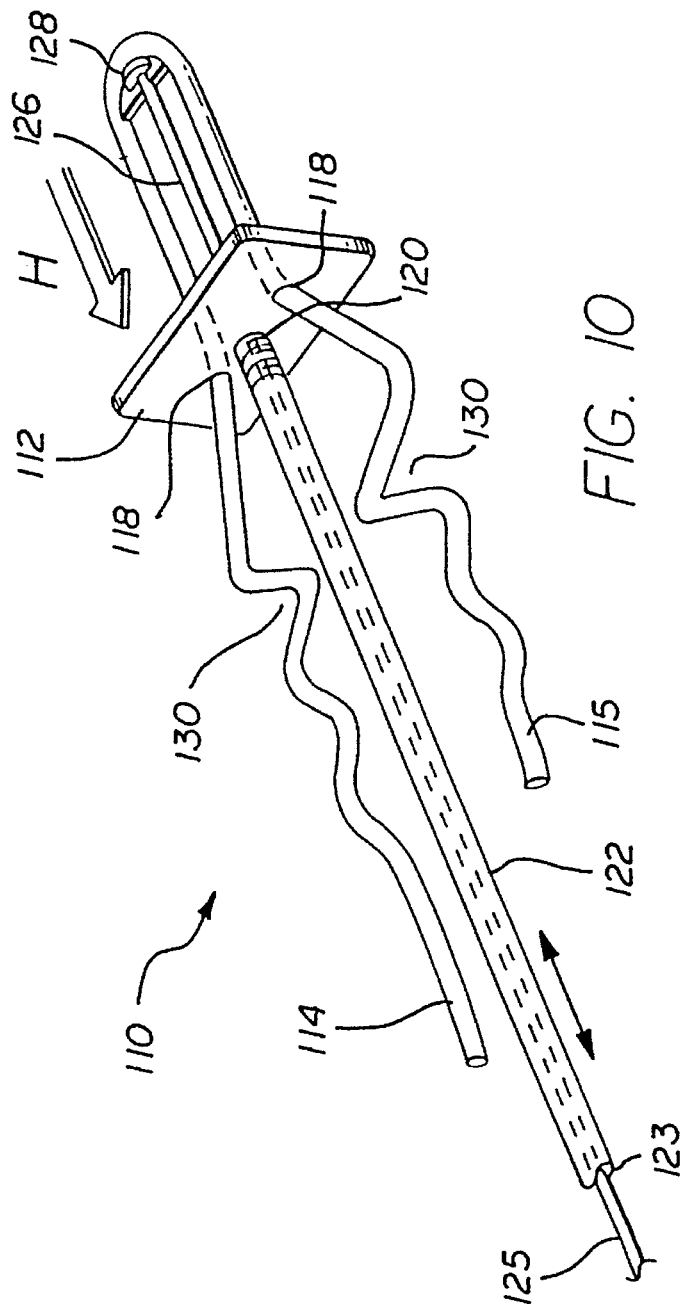
FIG. 8
FIG. 10

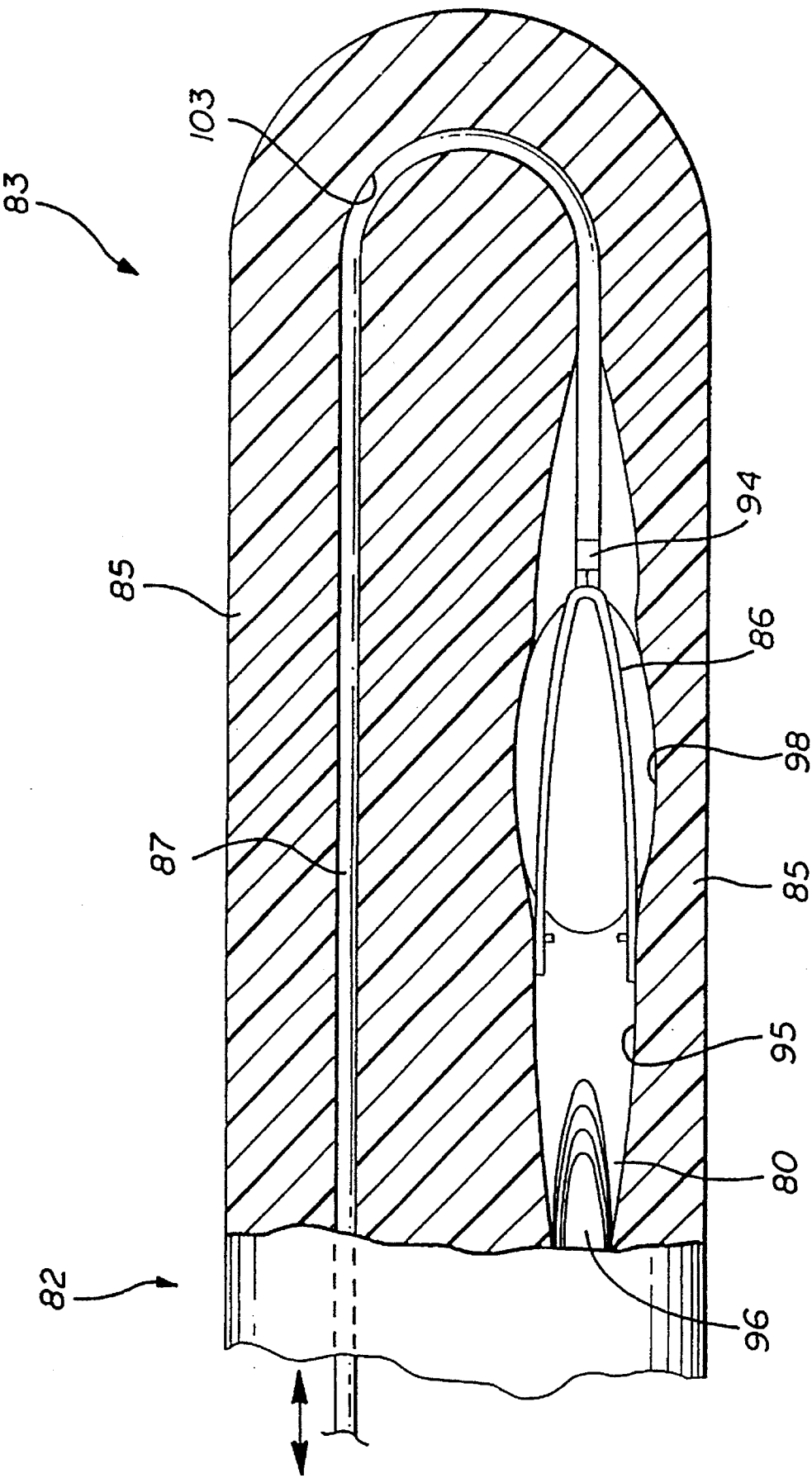

METHOD AND APPARATUS FOR MINIMALLY INVASIVE TREATMENT OF CHRONIC VENOUS INSUFFICIENCY

BACKGROUND OF THE INVENTION

This invention relates to the correction of incompetent venous valves or venous valvuloplasty, and more particularly to minimally invasive correction of venous insufficiency using a catheter based system to deploy an appliance or a prosthesis to repair or augment a valve in a vein.

The human venous system of the lower limb consists essentially of the superficial venous system and the deep venous system with perforating veins connecting the two systems. The superficial system includes the great saphenous vein and the small saphenous vein. The deep venous system includes the anterior and posterior tibial veins which unite to form the popliteal vein which in turn becomes the femoral vein when joined by the small saphenous vein. The venous systems contain a plurality of valves for directing blood flow to the heart.

Venous valves are usually bicuspid valves, with each cusp forming a sack or reservoir for blood which, under pressure, forces the free edges of the cusps together to prevent retrograde flow of the blood and allow only antegrade flow to the heart. When an incompetent valve attempts to close in response to a pressure gradient across the valve, the cusps do not seal properly and retrograde flow of blood occurs. There are two chronic venous diseases in which incompetence of venous valves is thought to be an important factor in the pathophysiology. These are varicose veins and chronic venous insufficiency.

Chronic venous insufficiency is a problem caused by hydrodynamic forces acting on the lowest part of the body, the legs, ankles and feet. As the veins dilate due to increased pressure, the valves in the veins become less able to withstand the weight of the blood above them. This causes the veins to dilate further and the valves in the veins to fail. As they fail, the effective height of the column of blood above the feet and ankles grows longer, and the weight increases with an increase in the pressure exerted on the tissues of the ankle and foot. When the weight of that column reaches a critical point because of enough dilation and valve failures, the person begins to have ulcerations of the ankle which start deep and eventually come to the surface. These ulcerations are very difficult to heal because the weight of blood causing them still exists, with the tendency to enlarge the ulcer, and because they are deep, often to the bone.

Chronic venous insufficiency consists of hypertension of the lower limb in the deep, perforating and often superficial veins with associated pigmentation, pain, swelling and ulceration. Existing treatments for chronic venous insufficiency are less than ideal. The only therapies currently available include elevation of the legs for twenty minutes every two hours, elastic support hose to compress the veins externally and surgical repair or replacement of the valves by grafting vein from the person's arm into the leg. These methods are variably effective. Moreover, surgery has its associated complications with risk to life and is usually very expensive. Similarly, the palliative therapies require major lifestyle changes for the patient. Also, without repairing the valves, even if the ulcers are healed, the ulcers always recur unless the patient continues to elevate the legs and to use support hose continuously.

Chronic venous insufficiency is essentially caused by venous hypertension and chronic venous stasis due to valvular incompetence both of a primitive nature (or primary or essential or idiopathic) and of a secondary nature following past illnesses of the venous system (generally speaking, deep venous thrombosis or phlebitis). In the case of venous valvular incompetence, the doctor has no efficacious drugs at his disposal, and the surgeon does not have ready access to artificial venous valves; whereas, valves of various types for heart diseases, etc. have been available for many years. Some methods of valvular reconstructive surgery may allow the recovery of valvular function in certain cases. However, the use of reconstructive surgery is obstructed by the delicate nature and irreversible damage of the valvular structures.

The varicose vein condition consists of dilatation and tortuosity of the superficial veins of the lower limb and resulting cosmetic impairment, pain and ulceration. Primary varicose veins are the result of primary incompetence of the venous valves of the superficial venous system. Secondary varicose veins occur as the result of deep venous hypertension which has damaged the valves of the perforating veins, as well as the deep venous valves.

The initial defect in primary varicose veins often involves localized incompetence of a venous valve thus allowing reflux of blood from the deep venous system to the superficial venous system. This incompetence is traditionally thought to arise at the saphenofemoral junction but may also start at the perforators. Thus, gross saphenofemoral valvular dysfunction may be present in even mild varicose veins with competent distal veins. Even in the presence of incompetent perforators, occlusion of the saphenofemoral junction usually normalizes venous pressure.

The initial defect in secondary varicose veins is often incompetence of a venous valve secondary to hypertension in the deep venous system. Since this increased pressure is manifested in the deep and perforating veins, correction of one site of incompetence could clearly be insufficient as other sites of incompetence will be prone to develop. However, repair of the deep vein valves would correct the deep venous hypertension and could potentially correct the secondary valve failure. Apart from the initial defect, the pathophysiology is similar to that of varicose veins.

Prior art prostheses include artificial venous valves and artificial valves for the heart and other anatomy which are adaptable for use in a vein. One such disclosed venous valve is comprised of an annular support member or ring defining an opening therethrough, including leaflets hingedly attached to the support ring for opening and closing the support ring opening in a manner permitting substantially unidirectional flow therethrough. Such valves are designed to be sutured or sewn into place within a blood vessel during a lengthy open surgery. The support ring of the valve is secured within a flexible fabric tube at a location generally medially of the tube. The blood vessel then is completely severed to provide two free ends; and each end of the fabric tube, within which the valve is secured, is sutured or sewn to a corresponding end of the free blood vessel to effectively splice the blood vessel.

Such prior art valves are likely to result in clotting of blood about the support member of the valve. Such clotting is, of course, undesirable and may be promoted by the fabric tube commonly utilized when suturing the valve into place. In particular, the fabric of the tube normally defines regions or voids within which blood is permitted to accumulate and clot. Furthermore, the fabric of the tube and support ring may provide gaps or spaces between the outer surface of the support ring and the inner wall of the fabric tube. Such gaps may cause the buildup of blood, thereby promoting clotting.

SUMMARY OF THE INVENTION

Briefly, and in general terms, the present invention provides a much less painful, less expensive and faster method for solving the underlying problems of venous valve insufficiency and uses a unique repair system, including a delivery catheter for placement of an appliance or a prosthesis. The system and method of the invention eliminate the need for open surgical valve repair procedures, obviate the need for arm vein transplantation into the leg, and allow patients to return to their former active lifestyles without the limitations currently associated with the treatment of this condition. For the sake of convenience, the invention will be described in relation to the correction of incompetent valves in the venous system of the lower limb in man; however, it is to be understood that the invention is not limited thereto.

The procedure for repair of incompetent venous valves may be accomplished by any qualified physician under fluoroscopic observation. First, the skin on the patient's ankle is cleaned and disinfected. A needle is inserted into the saphenous vein at the ankle and a wire is threaded through the needle as per the Seldinger technique. Alternatively, a cutdown to the saphenous vein is performed.

Once access to the vein is obtained as above, a delivery catheter is placed into the vein either over a wire or directly. The catheter is used to inject x-ray contrast material so that the venous valves can be identified. The catheter is moved up the vein toward the heart and is positioned at the level of the first functional valve or as far as the femoral vein. If the Seldinger technique is used, the wire would first be placed up to the femoral vein and the catheter would then be passed over the wire as described above.

Once the incompetent valve to be repaired is identified by injected contrast through the delivery catheter and the catheter is positioned at that valve, a clip appliance is deployed from the catheter and affixed to the valve. More than one clip may need to be placed. The catheter may contain more than one clip, or may have an integral clip making up its tip, so that a new catheter would be used for each clip placed and for each valve repaired. Alternatively, a prosthesis, such as an artificial valve, may be deployed from the catheter.

After the clip is placed, the delivery catheter is positioned proximate the next venous valve to be repaired. All valves may be repaired, or selective valves may be repaired. If the catheter design is a single clip type, then the wire and catheter is positioned proximate the next valve. The wire is left at that level in the vein while the catheter is removed. Another catheter and clip assembly is then placed over the wire with a repeat of the above procedure. If a catheter containing multiple clips is used, then the catheter is merely positioned at each valve wherein another clip appliance is deployed.

The delivery catheter is repositioned and clip appliances are deployed on sequentially lower valves until all desired valves are repaired and functionally competent. Valve competence may be determined by contrast injection or Doppler probe measurement. A competent, functioning valve demonstrates Doppler flow toward the heart with leg compression at the calf, but no flow in the reverse direction past the repaired valve with compression of the thigh. Once each valve is repaired, the wire and catheter are completely removed from the patient's leg.

Alternatively, a prosthesis, such as a replacement valve, or a natural or processed replacement vein may be placed by a catheter system. The prosthesis may be deployed similar to the clip appliance. Likewise, the replacement vein is placed at the proper position within the patient's vein and affixed with a stent having spikes or a similar attachment system. If necessary, the prosthesis, vein and stent are expanded and secured within the lumen of the vein by a balloon, spring or other method.

The clip appliance is made of a biocompatible material, such as a polymer, metal or fabric. The clip is constructed so that it will fit on or within the delivery catheter. The clip is configured with spreadable legs so as to fit over both sides of the venous valve. The clip is further configured to close either by a spring action or by compression so as to lock the legs together over the venous valve. The clip may have a single set of legs or may have multiple sets of legs. Conversely, the appliance could be staple-like and pierce or go through the valve as opposed to over the top of the valve leaflets.

The delivery catheter of the present invention is configured to position the appliance or prosthesis within the vein proximate the venous valve to be repaired. The catheter is capable of twisting or otherwise moving to allow for proper placement of the appliance or prosthesis. In addition, the catheter prevents the appliance or prosthesis from being inadvertently released into the bloodstream of the vein, etc. The catheter may be further configured for expanding or compressing a clip appliance, aligning the clip on each valve and assuring that the clip is securely fastened to the valve. Also, the delivery catheter tip would actually be the clip and would be disconnected from the rest of the catheter after appropriate placement. The catheter also may be configured to deliver x-ray contrast material. The delivery catheter, guide wire and appliance or prosthesis should be constructed of materials which would allow their visualization under fluoroscopy, x-ray, ultrasound or other imaging techniques.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIG. 2 is a plan view of a clip appliance of the present invention secured to the distal end of a delivery catheter.

FIG. 3 is a perspective view of the clip appliance and delivery catheter of FIG. 2.

FIG. 8 is a plan view of an alternative embodiment of the clip appliance of the present invention shown with a gripping device.

FIG. 9 is a partial cross-sectional view of the clip appliance and gripping device of FIG. 8 configured within the distal end of a delivery catheter.

FIG. 10 is a plan view of an alternative embodiment of the clip appliance of the present invention shown with a locking plate and delivery catheter.

DETAILED DESCRIPTION OF THE PREFERRED EMBODIMENTS

Figure 1:
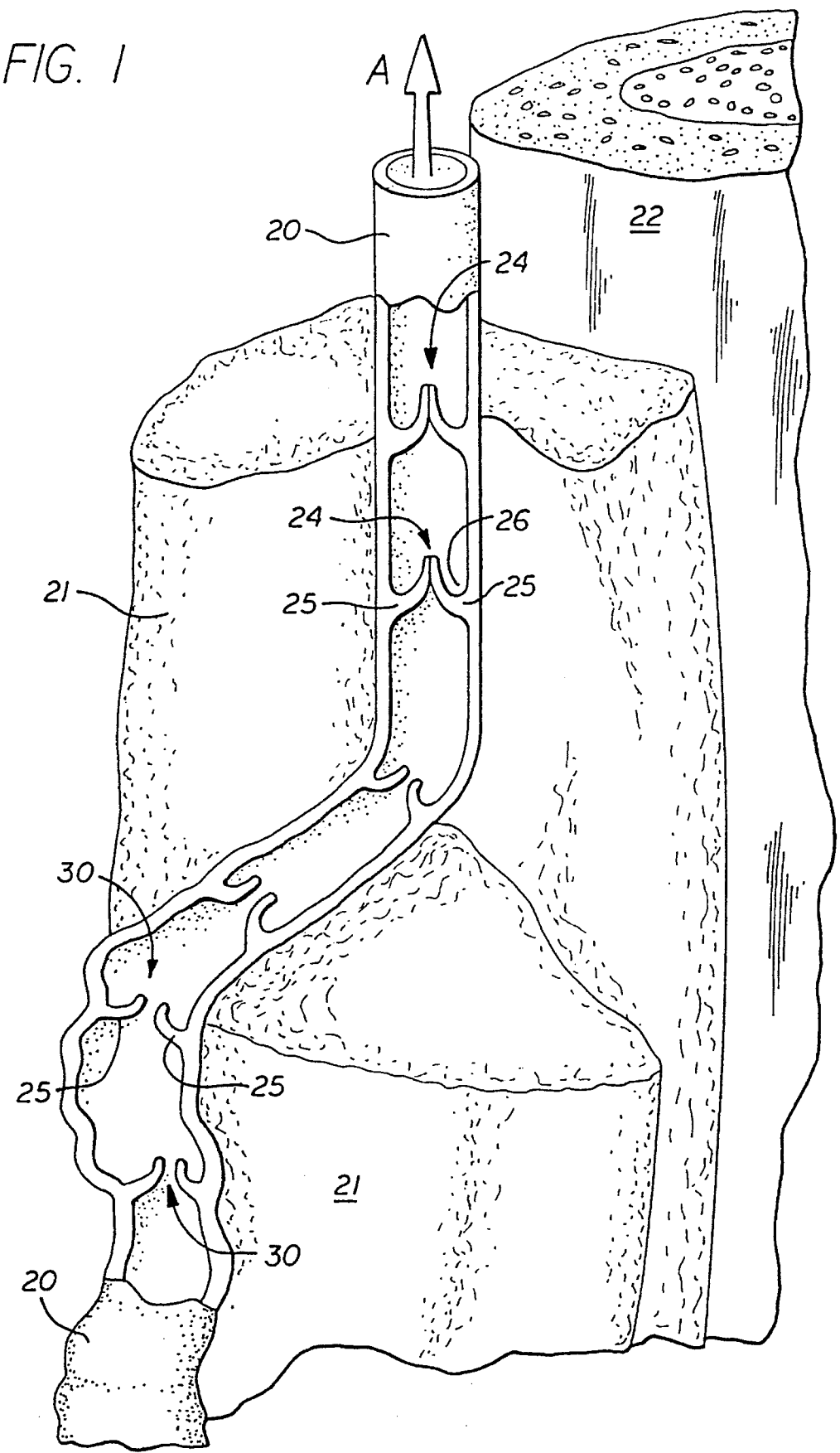
FIG. 1 shows a perspective view in partial cross-section of a vein having both competent and incompetent valves.

As shown in the exemplary drawings, the invention is embodied in a clip appliance 15 and delivery catheter 16 for use in a vein 20 for minimally invasive treatment of chronic venous insufficiency. As shown in FIG. 1, venous valves are usually bicuspid valves and are disposed within muscle tissue 21 and may be deep near a bone 22. In a normal and competent valve 24, each cusp 25 forms a sack or reservoir 26 for blood which, under pressure, forces the free edges of the cusps together to prevent retrograde flow of the blood and allow only antegrade flow to the heart (Arrow A). When an incompetent valve 30 attempts to close in response to a pressure gradient across the valve, the cusps do not seal properly and retrograde flow of blood occurs.

In accordance with the present invention, an appliance or prosthesis 15 is positioned by the delivery catheter 16 within the vein 20 adjacent an incompetent valve 30. The catheter is used to position an appliance so as to close the cusps 25 of the venous valve or otherwise reconstruct the valve to return it to its normal and competent function. Similarly, the catheter may be used to deliver a prosthesis, such as an artificial valve, proximate an incompetent valve or between incompetent valves so as to prevent retrograde flow of the blood moving through the vein. Thus, the system and method of the invention eliminate the need for open surgical valve repair procedures, such as vein transplantation into the leg, and allow patients to return to their former active lifestyles without the limitations currently associated with the treatment of chronic venous insufficiency.

As shown in FIG. 2, an embodiment of the appliance comprises a clip 15. The clip appliance comprises a first leg 40 connected to a biasing member 41. The biasing member is connected to a second leg 42, which is shorter than the first leg. The purpose of having a longer first leg is to ensure that the first leg enters one side of the cusp 25 of the incompetent valve 30 prior to inserting the second leg into the other cusp of the valve. The legs have serations or bends 44 which assist the clip in gripping the valve cusps.

The clip appliance 15 further comprises an adjustment mechanism 50 consisting of a screw-like member 52 attached to a cord 53 which is secured to the first leg 40 and the second leg 42. The delivery catheter 16 is used to manipulate the clip appliance through the anatomy and activate the adjustment mechanism. The catheter is removably secured by threads or other means to the clip at the proximal end 54 of the adjustment screw. As the adjustment screw is rotated (Arrow B), the cord shortens, thereby moving the first leg and the second leg closer together (Arrow C). Continued rotation of the adjustment screw in one direction (e.g., counterclockwise) will move the legs in close proximity to each other.

The clip appliance 15 further comprises a locking mechanism 55. The locking mechanism includes a locking hook 56 fixed on the second leg 42. The hook is configured to be secured over the first leg 40. As the adjustment mechanism moves the first leg closer to the second leg, the locking hook and first leg engage, thereby holding the legs of the clip appliance together in position. When the clip legs are in the closed position, the cusps 25 of the incompetent valve 30 are brought closer together to ensure competency of the valve. Likewise, the walls of the vein are brought closer together along the axis of the valve perpendicular to the direction of the clip closing. Once the lock mechanism is engaged, the delivery catheter 16 may be rotated in the opposite direction (e.g., clockwise) to release the clip appliance from the catheter.

In an alternative embodiment of the clip device, the adjustment means may comprise of a small diameter winder or screw member (not shown). The function of the smaller winder is basically the same as described heretofore, such that turning the winder causes the legs of the clip device to move together and for the locking mechanism to engage. The smaller winder, however, is adapted to be used with a smaller diameter catheter and requires less torque and more winding to close the legs.

As depicted in FIG. 3, the delivery catheter 16 of the present invention includes an elongate tubular member 60 configured for traversing the vein of a human patient. The catheter may be comprised of various materials which are biocompatible with the human anatomy. Such materials include stainless steel, PEBAX, and similar plastics. Such plastics may be injected or otherwise made with radiopaque material for visualization under fluoroscopy. In addition, radiopaque markers 62 may be embedded or otherwise secured to the catheter for observation under x-rays for fluoroscopy. For ease of traversing the vein, the catheter may be configured with an outer sheath (not shown). Such an outer sheath is configured to cover the distal end 65 of the catheter and the appliance or prosthesis, and is coaxial and separately retractable from the elongate tubular member 60.

The distal end 65 of the delivery catheter 16 is threaded or otherwise configured so as to engage the proximal end 66 of the adjustment mechanism of the clip device. The catheter may be turned, twisted and torqued from the proximal end 66. When the delivery catheter is engaged with the clip appliance 15, turning the proximal end of the catheter rotates its distal end, thereby rotating the adjustment screw 52 or disengaging the catheter from the clip. The proximal end of the catheter may include a "T-handle" 68 for ease of use by the surgeon. Similarly, the proximal end may be configured with a releasable locking mechanism to secure the outer sheath to the elongate tubular member 60. Alternatively, the distal end of the catheter is configured to deploy other prosthesis or appliances and the proximal end is similarly configured.

FIGS. 4–7 detail the method of the present invention for minimally invasive valvuloplasty for treatment of chronic venous insufficiency using the clip appliance 15 and delivery catheter 16 of FIGS. 2 and 3. Alternatively, the method is contemplated to be used with any suitable appliance or prosthesis for repair, reconfiguration or replacement of incompetent venous valves. In particular, the method of deploying a prosthesis is especially suited for deploying and implanting one or more natural or artificial venous valves.

To start the procedure, the patient is placed onto a gurney or procedure table (not shown) with the feet dependent to fill the veins of the leg. The ankle of patient is prepped with antiseptic solution. The ankle is tourniqueted with a band and the long saphenous vein is entered with an 18# or similar needle. A cutdown could also be performed rather than using the needle to enter the vein. The tourniquet is then removed.

A guide wire (not shown) is inserted into the vein 20 according to the well known and practiced Seldinger technique and the needle is removed. The wire is advanced to the level of the incompetent valve 30 which is to be repaired. Alternatively, the delivery catheter could be passed within the vein after insertion through the skin, without the need to advance the wire to that level. Fluoroscopy, x-ray, ultrasound, or a similar imaging technique is then used for specific placement of the catheter and confirmation of position.

Figure 4:
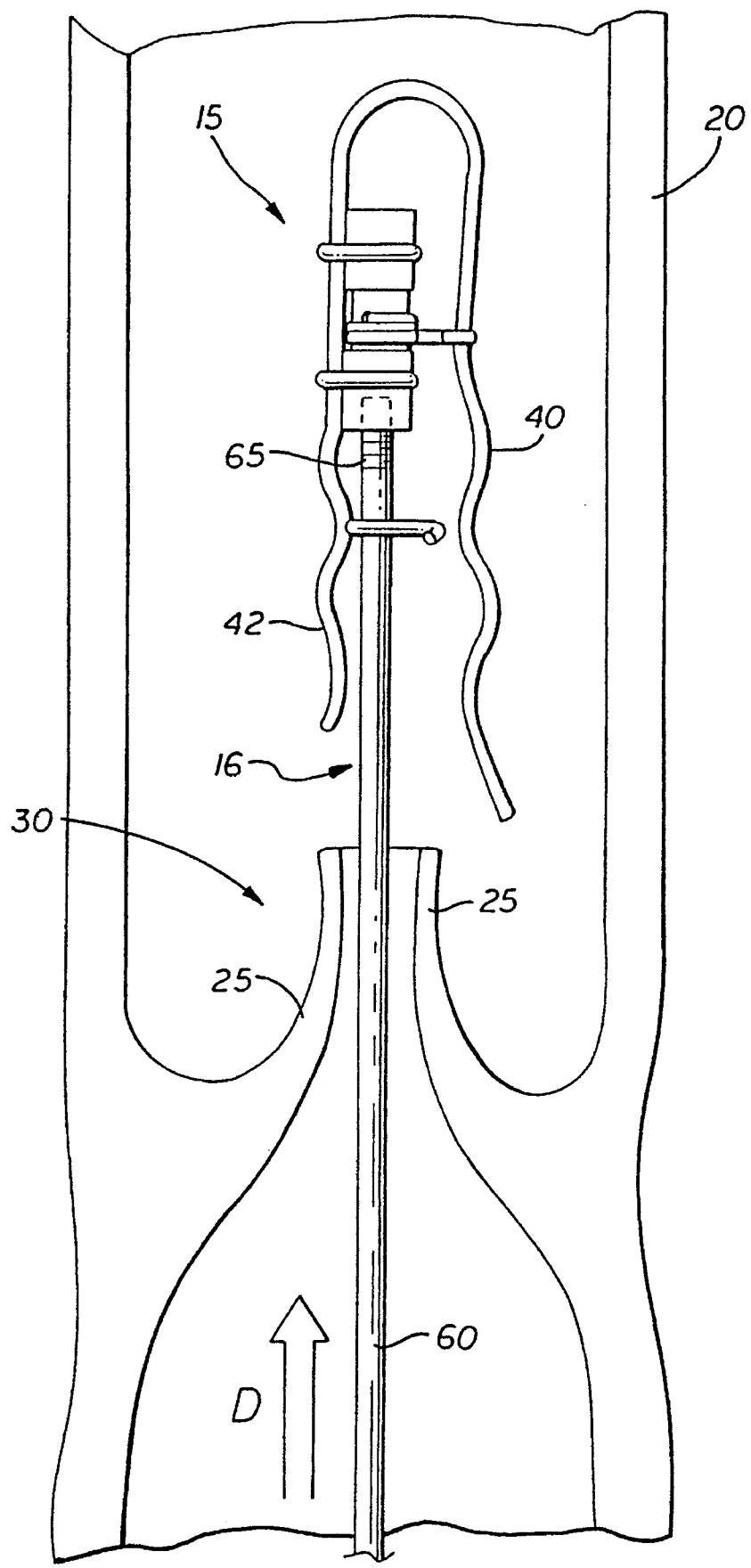
FIG. 4 is a partial cross-sectional view showing the clip appliance of FIG. 2 inserted into a vein proximate an incompetent valve.

Referring to FIG. 4, the delivery catheter 16 is then inserted upon the wire and is fed up the leg through the vein 20 into the femoral vein to the level of the most proximal incompetent valve 30. The distal end 65 of the catheter and the clip appliance 15 are advanced distally (Arrow D) through the vein while the outer sheath of the catheter (not shown) is held in place. This relative motion may be accomplished by a ratchet-like mechanism, by pushing the elongate tubular member 60 while holding steady the sheath, or by a cabling approach. As the appliance is advanced out of the sheath, the legs 40, 42 of the clip separate to a width greater than the distance between the valve cusps 25, as shown in FIG. 4. Other appliances or prostheses may be positioned in a like manner.

Figure 5:
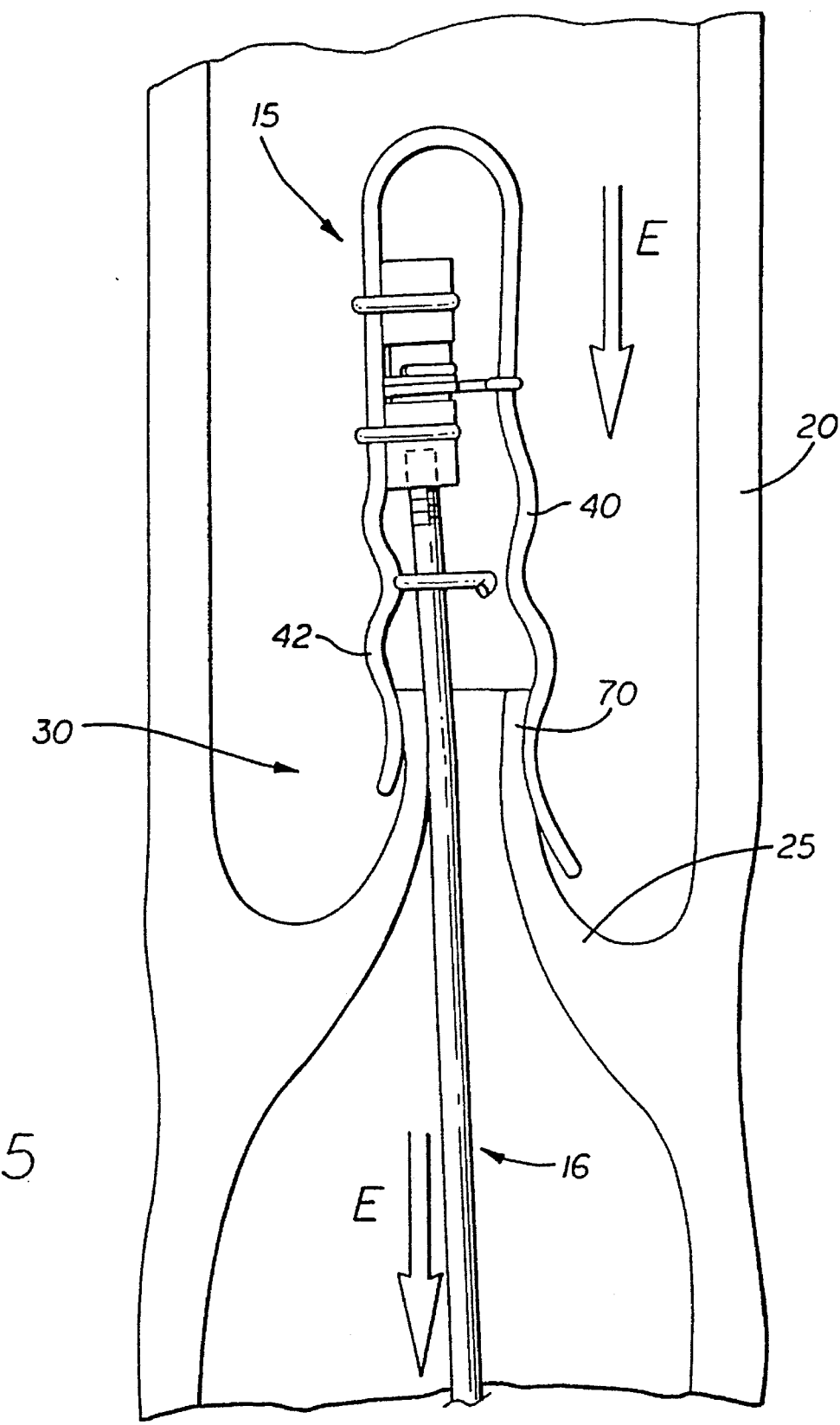
FIG. 5 is a partial cross-sectional view showing the clip appliance of FIG. 2 positioned with the legs of the appliance over the cusps of an incompetent valve.

As shown in FIG. 5, the entire delivery catheter 16 is then gently pulled in a proximal direction (Arrows E) within the vein 20 so that the legs 40, 42 of the clip appliance 15 catch on the outside of each 70 leaflet within the cusps 25 of the valve 30. In order to accomplish this, the patient may need to be placed into a Trendelenburg position or the veins may need to be exsanguinated using an elastic wrap around the leg and a tourniquet to prevent arterial inflow. The placement of the appliance or prosthesis may also be performed under direct visualization by an optical device such as a camera or fiber optic pathway or under fluoroscopy or x-ray or transillumination.

The clip appliance 15 may be positioned in the center of the width of the incompetent valve 30, on the edges or in between the center and the edges. Alternatively, the clip may be configured with multiple sets of legs which could be placed so that one set of clips is at each end of the valve width. Once the clip is positioned, the adjustment mechanism 50 is activated by turning the ratchet or screw-down assembly of the clip as in one embodiment (FIG. 2), by manipulating a cable within the catheter in another embodiment (FIG. 9), or by pulling down a plate as in another embodiment (FIG. 10).

Figure 6:
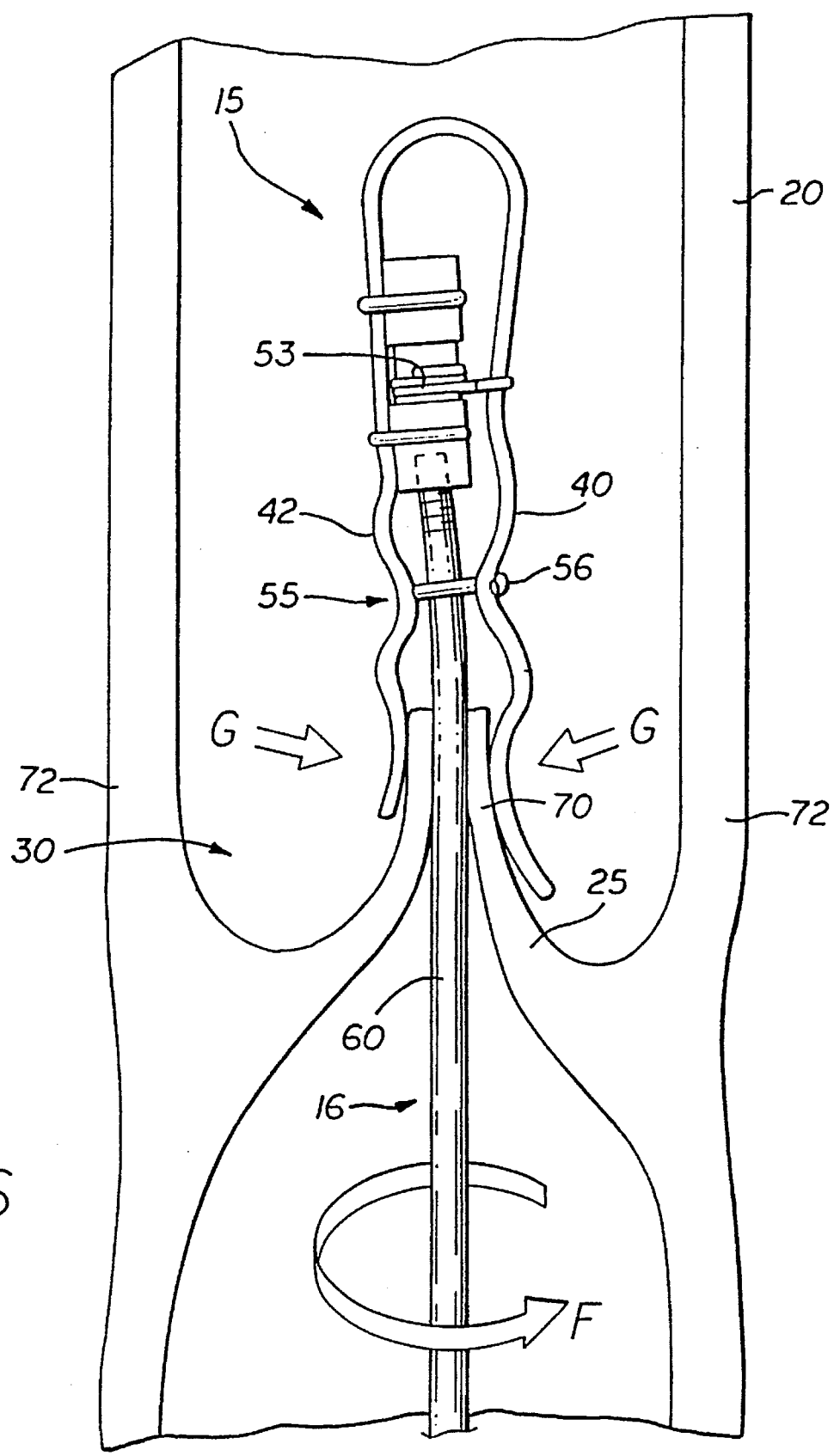
FIG. 6 is a partial cross-sectional view showing the clip appliance of FIG. 2 positioned with the legs of the appliance closed and locked onto the cusps of a valve.

Referring to FIG. 6, the delivery catheter 16 is rotated (Arrow F) to tighten the cord 53 and move the legs 40, 42 of the clip appliance 15 towards each other (Arrows G). The legs are closed until the hook 56 of the locking mechanism 55 engages the first leg. As the legs of the clip close, the leaflets 70 of the cusp 25 of the incompetent valve 30 are moved together. Likewise, the walls 72 of the vein 20 are also drawn together.

Figure 7:
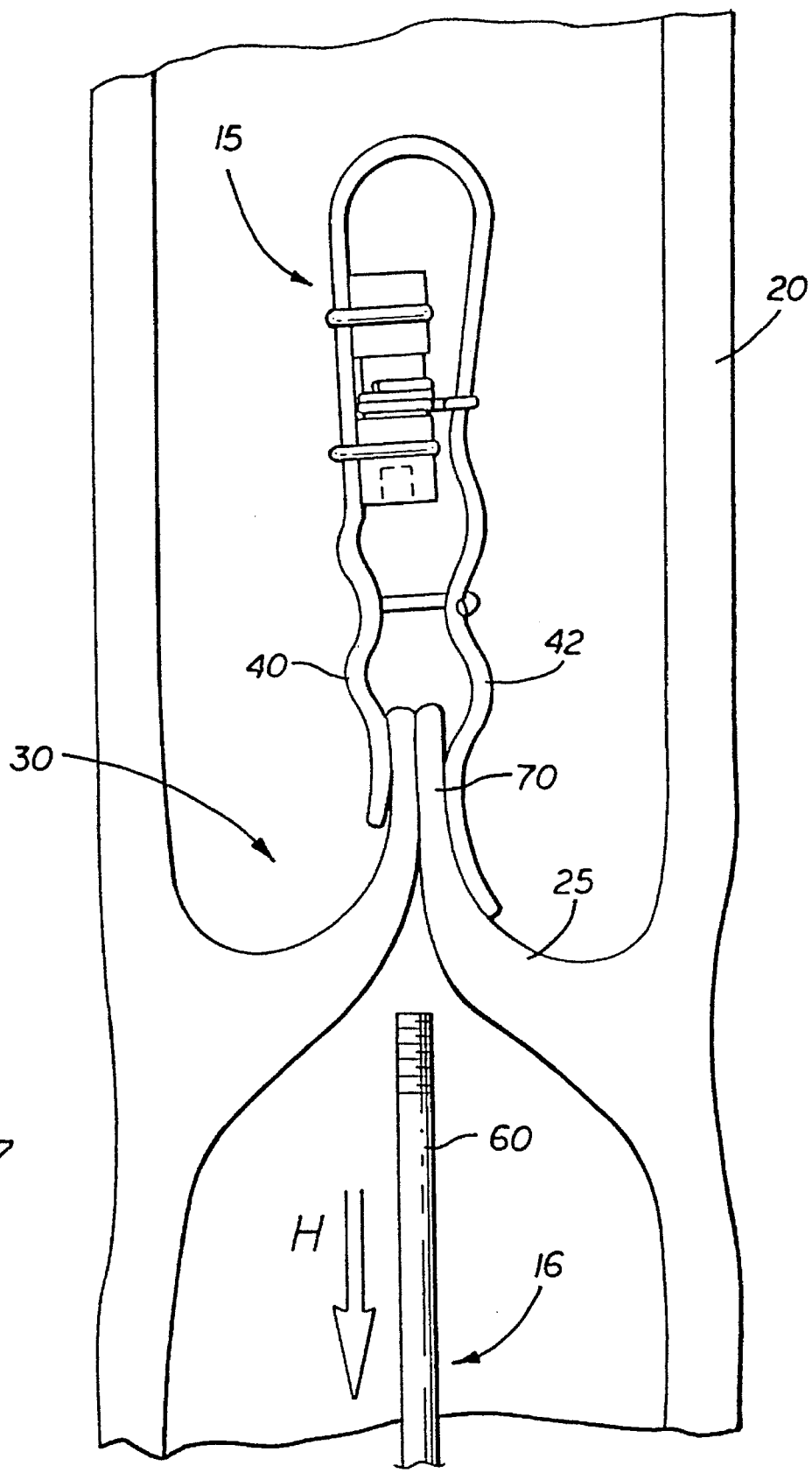
FIG. 7 is a partial cross-sectional view showing the clip appliance of FIG. 2 disengaged from the delivery catheter.

As shown in FIG. 7, the delivery catheter 16 is then disconnected either by unscrewing or otherwise unlocking the catheter from the clip appliance 15. The catheter is then moved proximally (Arrow H) within the vein 20 to clear the elongate tubular member 60 from the valve 30. As the catheter is removed from the valve, the legs 40, 42 of the clip push the leaflets 70 of the valve cusp 25 together until the valve is closed. At this point in the procedure, the valve is repaired and should be competent.

Once the clip appliance 15 is in place, another clip could be placed onto the same valve 30 if necessary. This might be done with the same delivery catheter 16 in the multiple-clip embodiment (FIG. 9) or by removing the "spent" catheter and inserting another in the same fashion as described heretofore. After sufficient clips have been placed and the catheter and wire are removed from between the repaired valve's cusps, the valve is tested using either an injection of contrast from a needle or catheter inserted proximal to the repair and with visualization under x-ray or by Doppler probe placed distal to the repaired valve. Compression of the leg or vein cephalad to the repair would demonstrate reverse flow should the valve be incompetent, and stopped flow if the valve were competent.

Next, the wire would be pulled back to the level of the next valve to be repaired, or the catheter would be placed at that level through the valve cusps as described heretofore. The same procedure would then be repeated for each subsequent valve repair. Once all necessary clips were applied, the catheter and guide wire would be removed. The access point of the vein would be sutured closed if a cutdown had been performed, or local pressure would be applied until bleeding was controlled. A bandage would then be applied. A pressure dressing may be necessary. Elastic support stockings may be applied subsequently.

FIGS. 8 and 9 show an alternative embodiment of the clip appliance 80 and a delivery catheter 82 having a distal end which includes a mechanism for deploying a plurality of clip appliances. The distal end of the catheter includes a capsule 85 sized sufficiently to hold a plurality of clips. The distal end further includes a "U" or "V" shape tweezers-like mechanism 86 for grasping the clips one at a time. The delivery catheter is configured with a cable 87 which extends from the proximal end of the catheter to the capsule. The cable's distal end is secured to the closed end of the tweezers and is disposed in a "U" shaped lumen 103 such that the open end of the tweezers faces proximally. The cable 87 is secured to the tweezers by a hinge 94 which allows manipulation of the tweezers from the proximal end of the cable. Thus, the cable and tweezers may be moved independent from the rest of the delivery catheter.

As shown in FIG. 8, each clip appliance 80 is configured in a "U" or "V" shape having a pair of legs 88 and 89 which are biased apart by the U-bend in the clip. Each leg of the clip has an indent 90 which mates with one of a pair of detents 92 on the legs of the tweezers 86. The tweezers are further provided with pads 93 which are sized and positioned to press the legs of the clip together when the tweezers are pressed against the clip. The first leg 88 of the clip appliance is provided with a niche 100 configured to accept a barb-like detent on the clip's second leg 89. When the legs of the clip are pressed together, the barb enters the niche, locking the clip legs together.

Referring to FIG. 9, the capsule 85 of the delivery catheter 82 is configured with a recess 95 having a proximal end in which a plurality of catheter appliances 80 may be placed for deployment. The tweezers 86 are movably disposed at the distal end of the capsule recess. The proximal end 96 of the capsule slot is tapered so that when the tweezers are moved proximally, the tweezers close around a clip, such that the tweezer detents 92 engage the clip indents 90.

A substantially oval slot or notch 98 is configured within a side of the recess in the capsule 85. The slot is shaped and dimensioned so that when the tweezers 86 are moved through the slot by manipulation of the cable 87, the tweezers open the legs 88, 89 of the clip appliance 80. Similarly, the slot is shaped such that when the capsule is moved proximally over the tweezers, the clip is closed and locked by the barb 101 entering the niche 100.

Thus, the clip appliance 80 may be secured to the cusp of a incompetent valve by manipulation of the cable 87 and tweezers 86. After deployment of a clip, the tweezers may be moved into the capsule 85 by manipulation of the cable. The hinge 94 is configured to permit the tweezers to move in and out of the slot 98 as the capsule and tweezers are moved relative to each other. Once the tweezers are returned to the capsule, the delivery catheter 82 may be moved so that the slot is adjacent the next valve to be repaired.

An alternative embodiment of a clip appliance is shown in FIG. 10. The "U" shaped clip is configured with a plate 112 which is used to secure the legs 114,115 of the clip together. The first leg 114 is longer than the second leg 115 and both legs have serations or bends for gripping a cusp of a venous valve. The plate is configured with holes in which the legs of the clip are disposed. The plate is further configured with a threaded hole 120 for receiving the distal end of an elongate tubular member 122 of a delivery catheter. The elongate tubular member is configured with a central lumen 123 for slidably receiving a pusher rod 125.

The clip appliance 110 is positioned within a vein and over a incompetent valve by the delivery catheter as described heretofore. Once in position, the tubular member 122 is moved in a proximal direction and the pusher rod 125 is held fixed. Movement of the tubular member causes respective movement of the plate 112 (Arrow I). The bend of the clip appliance between the legs 114, 115 is configured with a cup 128 which receives the distal end 126 of the pusher rod. As the plate is moved proximal to the legs of the clip, the legs are pushed together. Each leg is configured with a large bend 130 which acts as a stop catch for the plate, and locks the legs together when the plate is moved into the stop catch. After the plate is positioned in the stop catch, the tubular member is unscrewed or otherwise released from the plate and the tubular member and pusher rod are moved proximally away from the valve.

As can be readily ascertained from the disclosure herein, the surgical procedure of the present invention is accomplished without the need for prolonged hospitalization or post-operative recovery. The novel apparatus and method allow for curative restoration of venous valvular function without the need for continued lifestyle changes, such as frequent leg elevation, the wearing of relatively uncomfortable elastic support stockings or prolonged treatment of recurrent venous stasis ulcers. The minimally invasive procedure provides for more rapid healing of foot ulcers than is currently possible because of the functional restoration of the valves. Moreover, the need for surgery of the arm and leg for transplantation of arm vein valves into the leg is no longer necessary.

The new efficacious procedure is expected to have much less morbidity, thereby making it possible that early treatment of venous disease at the stage of varicose veins or pain and swelling without the advanced stages of ulceration could be treated. This would allow early treatment and prevention of more serious complications such as ulceration, thrombophlebitis and thromboembolism. The cost of treatment and complications due to venous disease would be significantly reduced because there would be no need for hospitalization for this procedure and also by the reduced need for subsequent treatment and hospitalization which currently are needed due to the palliative nature of most of the current methods of therapy.

While several particular forms of the invention have been illustrated and described, it will be apparent that various modifications can be made without departing from the spirit and scope of the invention. Accordingly, it is not intended that the invention be limited, except as by the appended claims.

What is claimed is:

1. A method for treating chronic venous insufficiency using a minimally invasive catheter based system, the method comprising:

providing an appliance for repairing an incompetent valve in a vein and a catheter for delivering the appliance;

inserting the catheter and the appliance into a vein of a patient;

positioning the appliance proximate the incompetent valve; and deploying the appliance such that the valve is repaired to be substantially competent.

2. The method of claim 1, further comprising the step of securing the appliance to a valve within an inner lumen of the vein of the patient.

3. The method of claim 2, wherein the appliance includes a clip having adjustment means for securing the clip onto the valve of the vein and further comprises the steps of positioning the clip on the valve and using the adjustment means to secure the clip to the valve.

4. The method of claim 1, further comprising the steps of:

providing a plurality of appliances disposed within the catheter;

positioning the catheter at a second valve; and deploying an appliance at said second valve such that the second valve is repaired to become competent.

5. A system configured to be deployable intraluminally to repair an incompetent valve within a vein to competence, the system comprising:

a clip including a first leg, a second leg, and a junction connecting the first leg to the second leg; and a catheter including a distal end configured to be deployed intraluminally within a vein, the clip being positioned at the distal end of the catheter, wherein the clip is deployed to engage an incompetent valve in the vein to repair the valve to competence.

6. The system of claim 5, wherein the first leg includes a first plurality of bends, and the second leg includes a second plurality of bends, wherein the first and the second plurality of bends assist the clip in gripping the valve.

7. The system of claim 5, wherein the first leg is longer than the second leg.

8. The system of claim 5, wherein the distal end of the catheter includes a slot formed therein, the clip being positioned within the distal end, and the catheter applying force to the clip to cause the first leg to move towards the second leg so that the clip is adjusted into position through the slot to engage the incompetent valve to return the valve to competence.

9. An implantable appliance configured to be deployable via a catheter and configured to repair an incompetent valve within a vein to competence, the appliance comprising:

a clip having a first leg, a second leg, and a junction connecting the first leg to the second leg, the junction biasing the first leg away from the second leg;

a cord attaching the first leg to the second leg;

a rotating element attached to the cord at the second leg; and a latch having a first end and a second end, the second end of the latch being attached to the second leg, and the first end of the latch being configured to be secured to the first leg;

wherein applying a force to the rotating element of the first leg causes the cord to move the first leg closer to the second leg so that the latch can connect the first leg to the second leg, and the first leg and the second leg are adjusted into position at an incompetent valve in a vein to return the valve to competence.

10. The appliance of claim 9, wherein the first leg is longer than the second leg.

* * * * *